(12) United States Patent
Uznanski et al.

(10) Patent No.: US 8,430,826 B2
(45) Date of Patent: Apr. 30, 2013

(54) SPECIMEN RETRIEVAL APPARATUS

(75) Inventors: Margaret Uznanski, Great Neck, NY (US); Anthony Ceniccola, Hamden, CT (US)

(73) Assignee: Covidien LP, Mansfield, MA (US)

( * ) Notice: Subject to any disclaimer, the term of this patent is extended or adjusted under 35 U.S.C. 154(b) by 281 days.

(21) Appl. No.: 12/709,464

(22) Filed: Feb. 20, 2010

(65) Prior Publication Data
US 2010/0256523 A1 Oct. 7, 2010

Related U.S. Application Data

(60) Provisional application No. 61/157,262, filed on Mar. 4, 2009.

(51) Int. Cl.
*A61B 10/00* (2006.01)
(52) U.S. Cl.
USPC .......................................... 600/565; 606/114
(58) Field of Classification Search .................. 600/565; 606/114
See application file for complete search history.

(56) References Cited

U.S. PATENT DOCUMENTS

| | | |
|---|---|---|
| 4,531,522 A | 7/1985 | Bedi et al. |
| 5,176,687 A | 1/1993 | Hasson et al. |
| 5,190,542 A | 3/1993 | Nakao et al. |
| 5,190,561 A | 3/1993 | Graber |
| 5,224,930 A | 7/1993 | Spaeth et al. |
| 5,330,483 A | 7/1994 | Heaven et al. |
| 5,337,754 A | 8/1994 | Heaven et al. |
| 5,368,597 A | 11/1994 | Pagedas |
| 5,423,830 A | 6/1995 | Schneebaum et al. |
| 5,486,182 A | 1/1996 | Nakao et al. |
| 5,524,633 A | 6/1996 | Heaven et al. |
| 5,643,282 A | 7/1997 | Kieturakis |
| 5,735,289 A | 4/1998 | Pfeffer et al. |
| 5,779,716 A | 7/1998 | Cano et al. |
| 5,836,953 A * | 11/1998 | Yoon .............................. 606/114 |
| 5,853,374 A * | 12/1998 | Hart et al. ..................... 600/562 |

(Continued)

FOREIGN PATENT DOCUMENTS

| | | |
|---|---|---|
| DE | 42 04 210 | 8/1992 |
| DE | 196 24 826 | 1/1998 |

(Continued)

OTHER PUBLICATIONS

Extended European Search Report dated Dec. 15, 2011 from European Patent Application No. EP 10251776.0 (3 pages).

*Primary Examiner* — Max Hindenburg
*Assistant Examiner* — Renee Danega (57) ABSTRACT

A specimen retrieval apparatus includes an elongated tubular member defining a lumen therethrough and having an end effector disposed at a distal end thereof. The end effector includes a shaft defining a longitudinal axis, the shaft including a lumen extending therethrough. The lumen of the shaft communicates with the lumen of the elongated tubular member. A suction member is disposed at a distal end of the shaft in communication with the lumen of the shaft. The suction member is configured to retain a tissue specimen thereon. A sleeve is disposed about the shaft and is movable with respect to the shaft from a proximal to a distal position. A specimen retrieval bag is coupled to the sleeve. The bag is deployable from an undeployed position wherein the bag is disposed about the sleeve to an extended position wherein the bag is deployed over the tissue specimen.

5 Claims, 8 Drawing Sheets

U.S. PATENT DOCUMENTS

| | | | |
|---|---|---|---|
| 5,921,979 A * | 7/1999 | Kovac et al. | 606/1 |
| RE36,974 E | 11/2000 | Bonutti | |
| 6,159,230 A * | 12/2000 | Samuels | 606/200 |
| 6,264,663 B1 | 7/2001 | Cano | |
| 6,270,505 B1 * | 8/2001 | Yoshida et al. | 606/127 |
| 6,350,267 B1 | 2/2002 | Stefanchik | |
| 6,383,195 B1 | 5/2002 | Richard | |
| 6,406,440 B1 | 6/2002 | Stefanchik | |
| 6,530,923 B1 | 3/2003 | Dubrul et al. | |
| 6,669,707 B1 | 12/2003 | Swanstrom et al. | |
| 6,692,499 B2 | 2/2004 | Tormalaet et al. | |
| 6,699,263 B2 | 3/2004 | Cope | |
| 7,021,316 B2 | 4/2006 | Leiboff | |
| 7,445,594 B1 | 11/2008 | Borst et al. | |
| 2002/0087190 A1 | 7/2002 | Benavitz et al. | |
| 2003/0004538 A1 | 1/2003 | Secrest et al. | |
| 2003/0105489 A1 | 6/2003 | Eichhorn et al. | |
| 2003/0139767 A1 * | 7/2003 | Jespersen | 606/205 |
| 2003/0149336 A1 | 8/2003 | Foley | |
| 2003/0149447 A1 | 8/2003 | Morency et al. | |
| 2003/0191497 A1 | 10/2003 | Cope | |
| 2004/0088003 A1 | 5/2004 | Leung et al. | |
| 2004/0122474 A1 | 6/2004 | Gellman et al. | |
| 2004/0138683 A1 | 7/2004 | Shelton et al. | |
| 2004/0176659 A1 | 9/2004 | Peng et al. | |
| 2004/0204723 A1 | 10/2004 | Kayan | |
| 2004/0220595 A1 | 11/2004 | Frazier et al. | |
| 2004/0230208 A1 | 11/2004 | Shayani | |
| 2004/0254609 A1 | 12/2004 | Esplin | |
| 2005/0085833 A1 | 4/2005 | Gedebou | |
| 2005/0203576 A1 | 9/2005 | Sulamanidze et al. | |
| 2005/0216040 A1 | 9/2005 | Gertner et al. | |
| 2005/0216042 A1 | 9/2005 | Gertner | |
| 2005/0240224 A1 | 10/2005 | Wu | |
| 2005/0267532 A1 | 12/2005 | Wu | |
| 2005/0273138 A1 | 12/2005 | To et al. | |
| 2006/0009786 A1 | 1/2006 | Bates et al. | |
| 2006/0025819 A1 | 2/2006 | Nobis et al. | |
| 2006/0030884 A1 | 2/2006 | Yeung et al. | |
| 2006/0058776 A1 | 3/2006 | Bilsbury | |
| 2006/0064126 A1 | 3/2006 | Fallin et al. | |
| 2006/0229675 A1 | 10/2006 | Novoa et al. | |
| 2006/0235446 A1 | 10/2006 | Godin | |
| 2006/0235447 A1 | 10/2006 | Walshe | |
| 2006/0253123 A1 | 11/2006 | Wilk | |
| 2006/0293709 A1 | 12/2006 | Bojarski et al. | |
| 2007/0135820 A1 | 6/2007 | Que et al. | |
| 2007/0208355 A1 | 9/2007 | Ruff | |
| 2007/0208377 A1 | 9/2007 | Kaplan et al. | |
| 2008/0033451 A1 | 2/2008 | Rieber et al. | |
| 2008/0071306 A1 | 3/2008 | Gertner et al. | |
| 2008/0215072 A1 | 9/2008 | Kelly | |
| 2008/0221588 A1 | 9/2008 | Hollis et al. | |
| 2009/0062618 A1 | 3/2009 | Drew et al. | |
| 2009/0182292 A1 | 7/2009 | Egle et al. | |
| 2009/0204130 A1 | 8/2009 | Kantsevoy et al. | |
| 2011/0190781 A1 | 8/2011 | Collier et al. | |
| 2011/0299799 A1 | 12/2011 | Towe | |

FOREIGN PATENT DOCUMENTS

| | | |
|---|---|---|
| EP | 2130483 | 12/2009 |
| WO | 97 26828 | 7/1997 |
| WO | 97 42889 | 11/1997 |
| WO | 00 12011 | 3/2000 |
| WO | WO 03/096907 A1 | 11/2003 |
| WO | 2004 002334 | 1/2004 |
| WO | WO 2007/149555 A2 | 12/2007 |
| WO | WO 2009/017680 A2 | 2/2009 |
| WO | WO 2010/099327 A1 | 9/2010 |

* cited by examiner

SPECIMEN RETRIEVAL APPARATUS

CROSS-REFERENCE TO RELATED APPLICATIONS

This application claims the benefit of U.S. Provisional Patent Application No. 61/157,262 filed on Mar. 4, 2009, the entire contents of which are incorporated by reference herein.

BACKGROUND

1. Technical Field

The present disclosure relates to a specimen retrieval apparatus, and more particularly, to a specimen retrieval apparatus for use in minimally invasive surgical procedures.

2. Background of Related Art

In minimally invasive surgical procedures operations are carried out within the body by using elongated instruments inserted through small entrance openings in the body. The initial opening in the body tissue to allow passage of instruments to the interior of the body may be a natural passageway of the body, or it can be created by a tissue piercing instrument such as a trocar, or created by a small incision into which a cannula is inserted.

Because the tubes, instrumentation, and any required punctures or incisions are relatively small, the surgery is less invasive as compared to conventional surgical procedures in which the surgeon is required to cut open large areas of body tissue. Therefore, minimally invasive surgery minimizes trauma to the patient and reduces patient recovery time and hospital costs.

Minimally invasive procedures may be used for partial or total removal of body tissue or organs from the interior of the body, e.g. nephrectomy, cholecystectomy, lobectomy and other procedures including thoracic, laparoscopic and endoscopic procedures. During such procedures, it is common that a cyst, tumor, or other affected tissue or organ needs to be removed via the access opening in the skin, or through a cannula. Various types of entrapment devices have been disclosed to facilitate this procedure. In many procedures where cancerous tumors are removed, removal of the specimen in an enclosed environment is highly desirable to prevent seeding of cancer cells.

In minimally invasive thoracic surgery, access to the thoracic cavity is limited as well as maneuverability within the cavity as the access port is placed between the confined space between a patient's ribs. Such procedures, commonly referred to as video assisted thoracoscopic surgery (VATS), aim to reduce patient recovery time by accessing the thoracic cavity through the natural intercostal space without spreading the ribs as in open procedures. This restricted access can sometimes cause problems when removing large specimens. Moreover, in such procedures, e.g. thoracoscopic wedge resection and lobectomy, it is often necessary to remove a portion of the lung and retrieve it relatively intact for pathology. It is also important that the specimen be sufficiently contained to prevent seeding of cancer cells during manipulation and removal.

In designing such specimen retrieval instrumentation, a balance must be struck between the need to provide a retrieval apparatus with a strong enough containment bag to prevent tearing or rupture while providing sufficient rigidity to enable manipulation and removal. Another balance which needs to be achieved is to provide sufficient maneuverability while reducing tissue trauma, e.g. damaging lung tissue, during manipulation and removal. Additionally, the instrumentation on one hand should be able to be inserted through a small access incision or port while on the other hand able to accommodate a wide range of patient sizes and be able to easily remove large specimens and minimize risk of seeding.

It would therefore be advantageous to provide a specimen retrieval device for minimally invasive surgical procedures with increased maneuverability and which minimizes trauma to surrounding tissue and which successfully achieves the balance of competing factors enumerated above.

SUMMARY

In accordance with one embodiment of the present disclosure, a specimen retrieval apparatus is provided. The specimen retrieval apparatus includes an elongated tubular member having an end effector assembly disposed at a distal end thereof. A first lumen extends through the elongated tubular member. The end effector assembly includes a shaft defining a longitudinal axis and having a second lumen in fluid communication with the lumen of the elongated tubular member. A suction member is disposed at a distal end of the shaft and is in communication with the lumen defined through the shaft. The suction member is configured to retain a tissue specimen thereon. A sleeve is disposed about the shaft and is movable with respect to the shaft from a proximal position to a distal position. A specimen retrieval bag is coupled to the sleeve. The bag is deployable from a first position to an extended position. In the first position, the bag is disposed about the sleeve. In the extended position, the bag is deployed over the tissue specimen.

In some embodiments, the end effector assembly is articulatable with respect to the elongated tubular between a first position wherein the end effector assembly is substantially aligned with a longitudinal axis of the elongated tubular member and a second position wherein the end effector assembly is angled with respect to the longitudinal axis of the elongated tubular member.

In some embodiments, a vacuum assembly is disposed at a proximal end of the elongated tubular member to provide a suction force through the lumens of the elongated tubular member and the shaft and to the suction member to suction the tissue specimen to the suction member.

In some embodiments, the sleeve is rotatable with respect to the longitudinal axis of the shaft to close the bag and the bag is retracted to envelope the tissue specimen.

In accordance with another aspect of the present disclosure, a specimen retrieval apparatus including a shaft and a specimen retrieval bag is provided. The shaft has a proximal end, a distal end and a lumen extending therethrough. The bag is at least partially disposed within the shaft. The bag includes a pre-formed glove portion extending distally from the shaft. The pre-formed glove portion includes first and second fingers configured to accommodate first and second jaws of a surgical grasper. The pre-formed glove portion is further configured to permit the surgical grasper to grasp a tissue specimen when disposed therein. The bag is deployable from the shaft over the tissue specimen grasped by the surgical grasper upon proximal translation of the shaft with respect to the bag.

In some embodiments, the bag includes an expandable ring disposed about an open end of the bag. The expandable ring is configured to expand the open end of the bag upon deployment of the bag from the shaft. The expandable ring may be formed from an expandable urethane foam. The bag may include one or more ribs extending therealong and configured to facilitate the expansion of the bag upon deployment from the shaft.

In some embodiments, the bag includes a cinch cord coupled to an open end of the bag. The cinch cord is selectively translatable to cinch the bag closed. The bag may also include a pre-printed barcode to assist in tracking the tissue specimen once it has been removed from the patient.

In accordance with another aspect of the present disclosure, a specimen retrieval apparatus is provided. The specimen retrieval apparatus includes an elongated tubular member defining a lumen therethrough. A vacuum assembly is disposed at a proximal end of the elongated tubular member for operation in at least one of a suction mode and a pressure mode. A suction cone is disposed at a distal end of the elongated tubular member and defines an aperture at an apex thereof in fluid communication with the lumen of the elongated tubular member. The suction cone is configured to suction a tissue specimen thereto when the two-way vacuum assembly is operating in the suction mode. A specimen retrieval bag is disposed at a distal end of the elongated tubular member and includes at least one chamber extending therethrough. The at least one chamber is in fluid communication with the lumen of the elongated tubular member and is inflatable to deploy the bag over the tissue specimen when the vacuum assembly is operating in the pressure mode.

In some embodiments, the suction cone is releasably coupled to the distal end of the elongated tubular member. A fluid-tight valve may be positioned at either the apex of the suction cone or at the distal end of the elongated tubular member, transitionable from an open position to a closed position for retaining the suctioned relationship between the suction cone and the tissue specimen.

In some embodiments, the bag includes a cinch cord coupled to an open end of the bag. The cinch cord can be selectively translatable to cinch the bag closed.

In some embodiments, the vacuum assembly is transitioned back to the suction mode once the bag has been closed to shrink-wrap the bag about the tissue specimen.

In accordance with yet another aspect of the present disclosure, a tissue retraction apparatus is provided. The tissue retraction apparatus includes an elongated shaft and a grasping portion disposed at a distal end of the elongated shaft. The grasping portion includes a grasping member having an adhesive patch attached thereto. Upon mating of the grasping member with tissue, the adhesive patch adheres the tissue to the grasping member. Thus, the tissue can be retracted by manipulating the tissue retraction apparatus.

In some embodiments, the grasping portion is articulatable with respect to the elongated shaft. In some embodiments, the adhesive patch is selectively detachable from the grasping member. The adhesive patch may also be made from a bioabsorbable material.

In some embodiments, the adhesive patch may be disengaged from the grasping member when the procedure is complete. The patch may be left adhered to the tissue to be absorbed by the tissue. Finally, the apparatus may be removed from the opening in tissue.

BRIEF DESCRIPTION OF THE DRAWINGS

Various embodiments of the subject apparatuses are described herein with reference to the drawings wherein.

DETAILED DESCRIPTION

Figure 1:
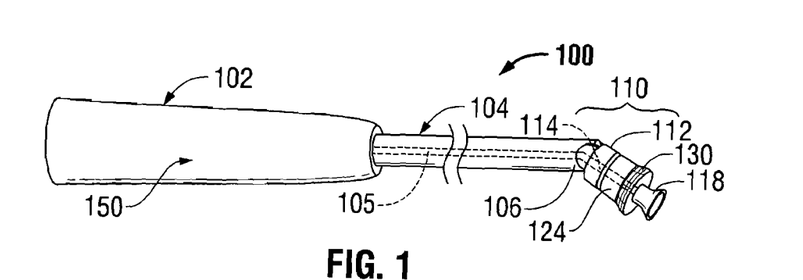
FIG. 1 is a side view of a specimen retrieval apparatus in accordance with the present disclosure.
Figure 2:
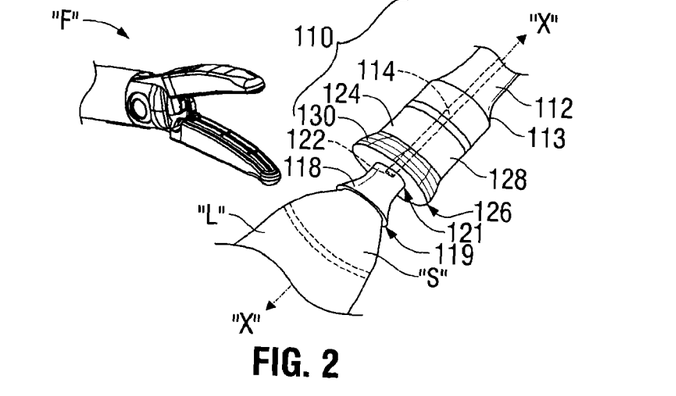
FIG. 2 is an enlarged, perspective view of an end effector of the specimen retrieval apparatus of FIG. 1 shown retaining a lobe of tissue in position for resection by a resection instrument.

Turning now to FIGS. 1 and 2, a specimen retrieval apparatus generally designated as 100 is shown including a handle assembly 102, an elongated tubular member 104 and an end effector assembly 110. The elongated tubular member 104 extends from the handle assembly 102 and includes a lumen 105 extending therethrough. The end effector assembly 110 is disposed at a distal end 106 of the elongated tubular member 104 and includes a shaft 112, a suction member 118, a translatable sleeve 124, and a specimen retrieval bag 130. The shaft 112 of the end effector assembly 110 includes a lumen 114 extending therethrough in fluid communication with the lumen 105 of the elongated tubular member 104.

End effector assembly 110 is articulatably coupled to the distal end 106 of the elongated tubular member 104 to permit articulation of the end effector assembly 110 with respect to the elongated tubular member 104. The end effector assembly 110 may be coupled to the elongated tubular member 104, for example, via a pin-aperture mechanism 140 (FIG. 3), allowing for one-dimensional articulation of the end effector assembly 110, via a ball and socket mechanism (not shown), allowing for 360° articulation of the end effector assembly 110, or by any other suitable mechanism. As can be appreciated, articulation of the end effector assembly 110 allows for increased maneuverability of the apparatus 100 within an internal body cavity.

Handle assembly 102 includes a vacuum assembly 150 disposed therein or, alternatively, is coupled to a remote, or separate vacuum assembly, for providing a suction force at the suction member 118. The handle assembly 102 may further include one or more controls (not shown), e.g., triggers, joysticks, and/or switches. The controls may be configured for activating the vacuum assembly 150, for articulating the end effector assembly 110 with respect to the elongated tubular member 104, for advancing the sleeve 124 of the end effector assembly 110, and/or for deploying the specimen retrieval bag 130.

The shaft 112 of the end effector assembly 110 defines a longitudinal axis "X." The suction member 118 extends from a distal end 113 of the shaft 112. The suction member 118 includes a funnel-shaped distal end 119 and a central aperture 122 defined at a proximal end, or apex 121 thereof. The aperture 122 of the suction member 118 communicates with the lumen 114 of the shaft 112, which, in turn, communicates with the lumen 105 of the elongated tubular member 104 such that, upon activation of the vacuum assembly 150, a suction force is provided to the suction member 118. The suction member 118 may be made from a flexible bio-material such that the suction member 118 may conform to a tissue specimen "S." The flexible, funnel-shaped suction member 118 facilitates a fluid-tight suction between the suction member 118 and a tissue specimen "S," as shown in FIG. 2.

The translatable sleeve 124 is positioned annularly about the shaft 112. The sleeve 124 is axially translatable with respect to the shaft 112 from a proximal, or retracted, position to a distal, or extended position. The specimen retrieval bag 130 is initially disposed annularly about a distal end 126 of the sleeve 124 and is thus translated simultaneously with the translation of the sleeve 124. One end 132 (FIG. 4B) of the bag 130 is sealingly engaged to the outer surface 128 of the sleeve 124. As shown in FIG. 2, the bag 130 is disposed in its initial rolled-up, or un-deployed state. Upon deployment, as will be described in greater detail below, the free (open) end 134 (FIG. 4B) of the bag 130 is extended distally to encapsulate the tissue specimen "S" retained in place by the suction member 118.

Figure 3:
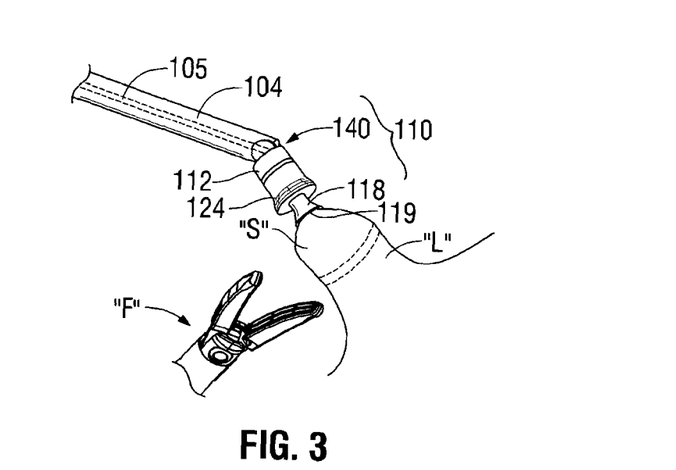
FIG. 3 is perspective view of the specimen retrieval apparatus of FIG. 1 shown articulated to retain the lobe of tissue in position.

With reference now to FIGS. 1-5B, the operation of specimen retrieval apparatus 100 will now be described. Initially, the vacuum assembly 150 is deactivated, the specimen retrieval bag 130 is in the rolled-up, or un-deployed state, and the sleeve 124 is in the proximal, or retracted position. The specimen retrieval apparatus 100 is inserted, lead by end effector assembly 110, through an access port (not shown) or opening in tissue and maneuvered for positioning adjacent the tissue specimen "S" to be removed. The end effector assembly 110 may be articulated, e.g., about pin-aperture mechanism 140, for such positioning as shown in FIG. 3. to increase the lateral mobility of the elongated tubular member 104.

With the suction member 118 positioned adjacent the tissue specimen "S" to be retrieved, the specimen retrieval apparatus 100 is moved such that the funnel-shaped distal end 119 of the suction member 118 contacts a surface of the tissue specimen "S," as shown in FIG. 3. As mentioned above, the flexible suction member 118 may conform to the surface geometry of the tissue specimen "S" upon contact of the suction member 118 with the surface of the tissue specimen "S."

At this point, the vacuum assembly 150 may be activated, e.g., by squeezing a trigger (not shown), to provide a suction force to the suction member 118. More particularly, a suction is created through the aperture 122 defined within the proximal end 121 of the suction member 118, through the lumen 114 of the shaft 112, and through the lumen 105 of the elongated tubular member 104. As the tissue specimen "S" is suctioned to the suction member 118, the flexible suction member 118 creates a fluid-tight seal about the tissue specimen "S" to retain the specimen "S". As can be appreciated, the flexibility of the suction member 118 helps maintain the fluid-tight suction between the tissue specimen "S" and the suction member 118, even where the tissue specimen "S" had a complex surface geometry.

With the tissue specimen "S" retained by the suction member 118, the end effector assembly 110 and/or the specimen retrieval apparatus 100 may be manipulated to maneuver the tissue specimen "S" into position. For example, as shown in FIGS. 2-3, the end effector assembly 110 may be articulated to position a lobe "L" of tissue for resection. The lobe "L" is retained in position and a surgical cutter "F" is inserted through a second access port (not shown) to resect the tissue specimen "S" from the lobe "L." Retraction of a lobe of tissue "L" is one example, however it is envisioned that specimen retrieval apparatus 100 may also be used to retract and retain other tissues, e.g., cysts, tumors, or other affected tissue or organ.

Figure 4A:
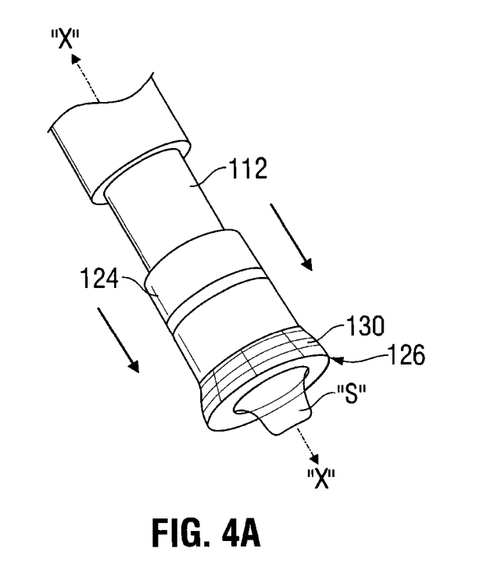
FIG. 4A is an enlarged, perspective view of the end effector of the specimen retrieval apparatus of FIG. 1 wherein a sleeve of the end effector assembly is advanced over the resected lobe of tissue.

After the tissue specimen "S" has been resected from the lobe "L" (or retained by suction member 118 where resection is not required), the tissue specimen "S" may be encapsulated by the specimen retrieval bag 130 for removal from the internal body cavity. The sleeve 124 is advanced from the proximal position to the distal position, as shown in FIG. 4A. As mentioned above, the handle assembly 102 may include controls for mechanically translating the sleeve 124 from the proximal position to the distal position or it may be manually advanced by an instrument inserted through another access port or opening. The sleeve 124 is advanced distally to surround the suction member 118. In the distal, or extended position, the distal end 119 of the sleeve 124 can optionally extend beyond the tissue specimen "S" retained by the suction member 118 such that the suction member 118 and the tissue specimen "S" are substantially surrounded by the sleeve 124.

Figure 4B:
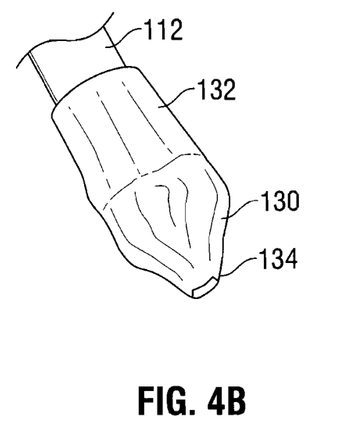
FIG. 4B is perspective of the end effector of the specimen retrieval apparatus of FIG. 4A where a specimen retrieval bag has been deployed and cinched closed around the resected lobe.

From this position, the bag 130 may be deployed, or unrolled from the distal end 126 of the sleeve 124. Deployment of the specimen retrieval bag 130 may be mechanically activated by a control (not shown) disposed on the handle assembly 102. Alternatively, the bag 130 may be deployed automatically upon distal translation of the sleeve 124. Alternatively, a surgical grasper, e.g., forceps "F," inserted through another access port or incision, may be used to draw the bag 130 over the tissue specimen "S". The bag 130 is deployed from the distal end 126 of the sleeve 124 and extends distally to fully encapsulate the tissue specimen "S," as best shown in FIG. 4B. Where required, the end effector assembly 110 may be articulated and/or manipulated to position the tissue specimen "S" within the bag 130.

Figure 5A:
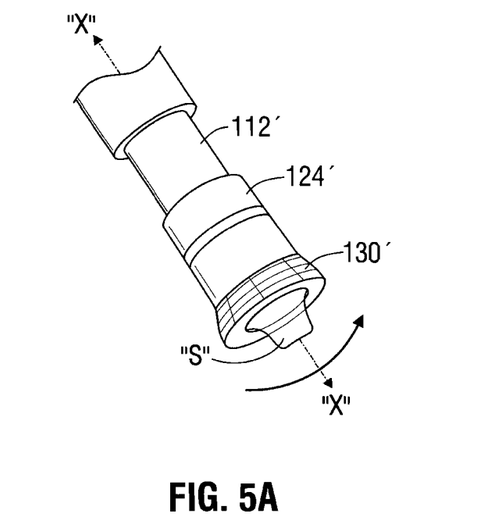
FIG. 5A is an enlarged, perspective view of the end effector of the specimen retrieval apparatus of FIG. 1 according to an alternate embodiment where the sleeve is rotated with respect to the resected lobe.
Figure 5B:
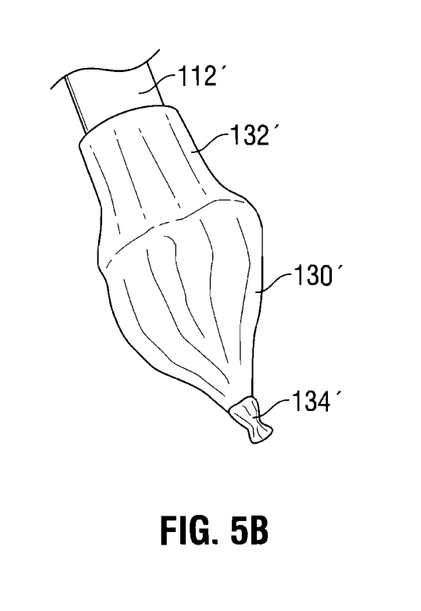
FIG. 5B is a perspective view of the end effector of the specimen retrieval apparatus of FIG. 5A where the specimen retrieval bag has been deployed around the resected lobe.
Figure 6:
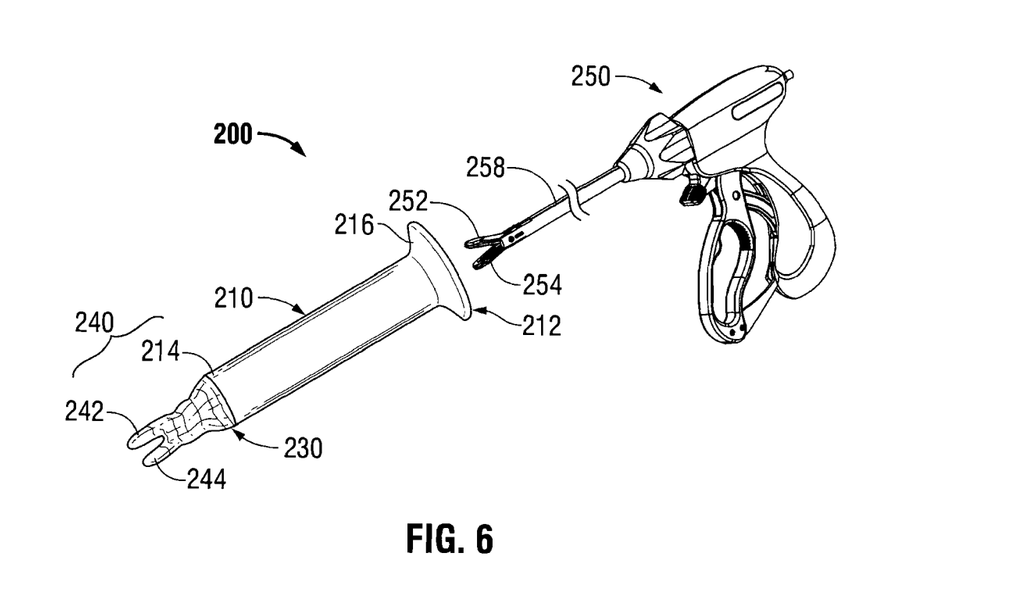
FIG. 6 is a perspective view of another specimen retrieval apparatus in accordance with the present disclosure.
Figure 7:
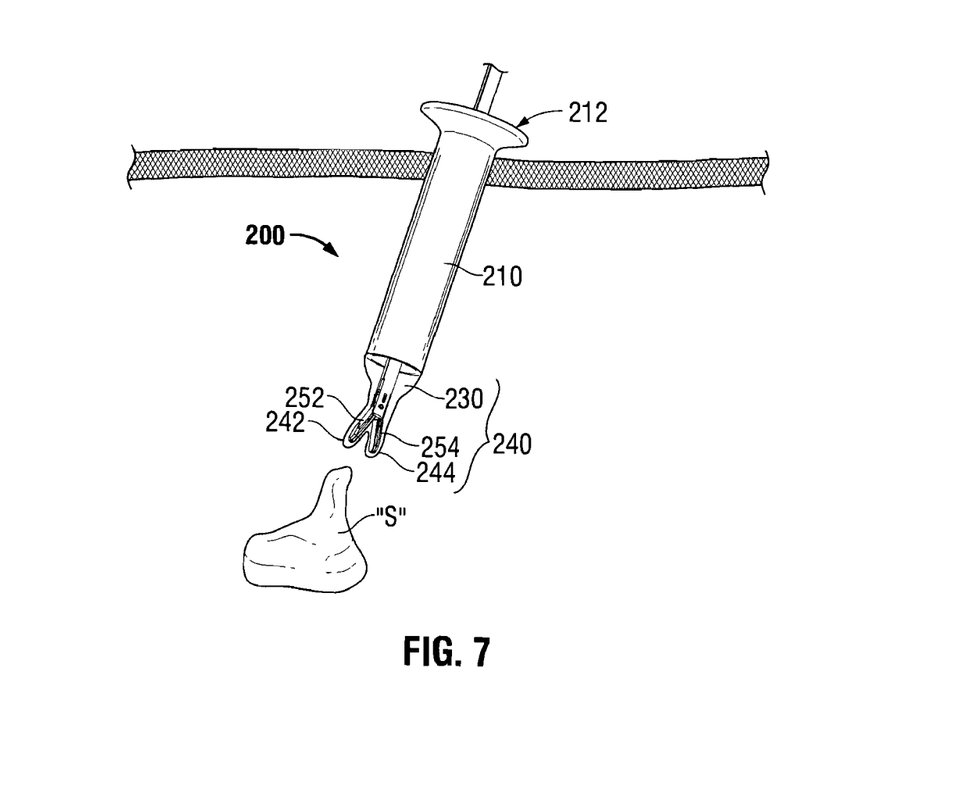
FIG. 7 is a side, cross-sectional view showing the specimen retrieval apparatus of FIG. 6 including a grasper inserted through a shaft of the specimen retrieval apparatus for manipulating a tissue specimen within the patient's body.

In some embodiments, as shown in FIG. 5A, the sleeve 124' may be rotated with respect to the shaft 112' about the longitudinal axis "X" of the shaft 112' to close the open end 134' (FIG. 5B) of the bag 130'. In this embodiment, upon deployment of the bag 130', the bag 130' is closed, and then retracted to encapsule the tissue specimen "S" therein. Alternatively, once the bag 130 has been deployed, a cinch cord (not shown) disposed about the open end 134 of the bag 130 may be used to close the bag 130. Further, the open end 134 of the bag 130 may be closed by any other suitable means, e.g., thermal sealing by the surgical forceps "F." The other end 132 of the specimen retrieval bag 130 remains sealingly engaged to the sleeve 124, as discussed above. Thus, once the open end 134 of the bag is closed, the bag 130 seals off the tissue specimen "S" from the internal body cavity.

The internal bag surface can be coated with a compliant or flowable coating, such as silicone, such that when the bag is rotated, cinched or otherwise closed, the coating achieves the fluid seal.

Once the tissue specimen "S" has been sealed within the bag 130, the vacuum assembly 150 may be deactivated, releasing the suction retaining the tissue specimen "S" to the suction member 118. Upon release of the suction, the tissue specimen "S" drops into the specimen retrieval bag 130, and the specimen "S" remains isolated from the internal body cavity due to the sealing engagement of the bag 130 with the distal end 126 of the sleeve 124 and due to the previously closed end 134 of the bag 130. With the tissue specimen "S" disposed within the sealed bag 130, the vacuum assembly 150 may be re-activated to suction out the fluids within the specimen retrieval bag 130. Suctioning the sealed bag 130 minimizes the volume within the bag 130 to facilitate removal. This feature also helps prevent "catching" of the bag 130 during removal. Further, encapsulating the tissue specimen "S" within a sealed environment inhibits seeding during the removal of the tissue specimen "S" from the body.

It is envisioned that the specimen retrieval bag 130 be made from a flexible, tear and puncture resistant bio-material. Transparent materials can also be utilized to permit visualization into and through the specimen retrieval bag 130, enabling the surgeon to visually verify the position of the tissue specimen "S" with respect to the specimen retrieval bag 130. It is also envisioned that the bag include a pre-printed bar code or other identification number 248 (see FIG. 10) to facilitate tracking of the specimen "S" once it has been removed from the body.

Turning now to FIGS. 6-10, another embodiment of a surgical retrieval apparatus is shown generally indicated by reference numeral 200. Surgical retrieval apparatus 200 includes a hollow shaft 210 and a specimen retrieval bag 230 initially disposed within the internal chamber 212 of the hollow shaft 210. The shaft 210 is preferably formed from a rigid or semi-rigid material, while the specimen retrieval bag 230 is preferably formed from a more flexible material. The specimen retrieval bag 230 is deployed distally from the shaft 210 upon proximal translation of the shaft 210 with respect to the bag 230. A pre-formed glove portion 240 of the bag 230 extends distally from the distal end 214 of the hollow shaft 210 when the bag 230 is positioned within the internal chamber 212 of the shaft 210. The surgical retrieval apparatus 200 is configured for insertion of a surgical grasper 250 through the internal chamber 212 of the shaft 210.

The specimen retrieval bag 230 may be made of a relatively thin, flexible bio-material that is preferably puncture and tear resistant. It is also envisioned that the bag 230 can be transparent to permit visualization of the tissue specimen "S" (FIG. 7) within the bag 230. The pre-formed glove portion 240 is integral with, or sealingly engaged with the bag 230 and includes first and second fingers 242, 244, respectively. Each finger 242, 244 is configured to accommodate a jaw 252, 254, respectively, of the surgical grasper 250. The pre-formed glove portion 240 can be formed from a more-rigid material than the bag 230 to retain the pre-formed glove shape to facilitate insertion of jaws 252, 254 therein. However, the pre-formed glove portion 240 is also somewhat flexible in response to the approximation of the jaws 252, 254, such that the tissue specimen "S" (FIG. 7) may be grasped therebetween.

The hollow shaft 210 includes a funnel-shaped proximal end 216 configured to guide the insertion of the surgical grasper 250 into the chamber 212 extending through the hollow shaft 210. The shaft 210 defines a length sufficient to provide access through the body tissue and into an internal body cavity, but not longer than a length of the shaft 258 of the surgical grasper 250 such that the jaws 252, 254 extend beyond the shaft 210 and into the pre-formed glove portion 240. The hollow shaft 210 has a relatively small diameter to permit insertion of the surgical retrieval apparatus 200 through small openings in tissue, with the specimen retrieval bag 230 retained within the shaft 210 in a compressed or collapsed state.

With reference now to FIGS. 7-10, the operation of surgical retrieval device 200 will now be described. Initially, the shaft 210 is inserted through an access port, or opening in tissue and positioned such that the pre-formed glove portion 240 of the retrieval bag 230 is disposed adjacent a tissue specimen "S" to be retrieved. With shaft 210 in position, a surgical grasper 250 (FIG. 6) is inserted into the chamber 212 through the proximal end 216 of the hollow shaft 210 until the jaws 252, 254 are disposed within the fingers 242, 244, respectively, of the pre-formed glove portion 240. With jaws 252, 254 disposed within the fingers 242, 244, respectively, the jaws 252, 254 may be approximated to grasp the tissue specimen "S" therebetween.

In some embodiments, the surgical grasper 250 includes a clip (not shown) disposed between the jaw members 252, 254. The clip is configured to snap closed upon approximation of the jaw members 252, 254 to clip the tissue specimen "S" to the specimen retrieval bag 230 disposed within the pre-formed glove portion 240. As can be appreciated, the clip would allow the operator to remove the surgical grasper 250 from the shaft 210, while maintaining the fixed engagement between the surgical retrieval bag 230 and the tissue specimen "S."

Figure 8:
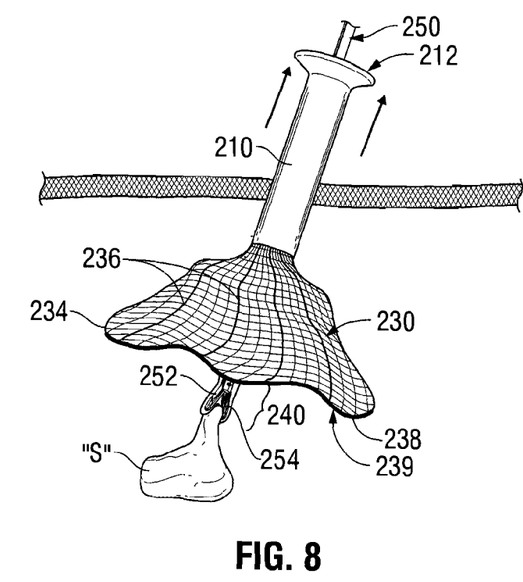
FIG. 8 is a side, cross-sectional view showing the shaft being translated proximally to deploy a specimen retrieval bag over the tissue specimen.

Once the tissue specimen "S" has been grasped by the surgical grasper 250, the specimen retrieval bag 230 may be deployed to encapsulate the tissue specimen "S." The hollow shaft 210 is translated proximally, as indicated by the arrows shown in FIG. 8, exposing the bag 230 from within the internal chamber 212 of the shaft 210. The bag 230 may include one or more flexible ribs 236 to facilitate the expansion upon deployment. Flexible ribs 236 may be biased toward an expanded position to retain the bag 230 in an expanded state upon deployment. Further, the bag 230 may include an expandable ring 239, expandable by a foam or fluid, at an open end 238 thereof to expand upon deployment of the specimen retrieval bag 230 and maintain the open end 238 of the bag 230 in an open position, thus providing a fixed opening into which the tissue specimen "S" may be manipulated. The expandable ring 239 provides structure to the open end 234 of the bag 230 to facilitate manipulation of the bag 230 over the tissue specimen "S." The ring 239 may be made from any suitable expandable foam, e.g., cellular urethane foam manufactured by PORON®.

Figure 9:
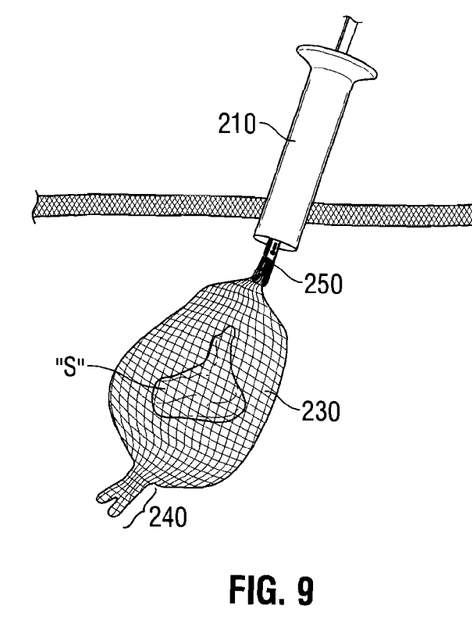
FIG. 9 is a side, cross-sectional view showing the specimen fully disposed within the bag in preparation for removal from the patient's body.

After the specimen retrieval bag 230 has been deployed over the tissue specimen "S," the grasper 250 may be used to maneuver the specimen "S" into the bag 230. Additionally, or alternatively, a second grasper (not shown) inserted though a second access port (not shown) may be used to draw the bag 230 over the specimen "S." Once the bag 230 has been drawn completely over the specimen "S," the bag 230 may be closed off for removal. In some embodiments, the open end 238 of the bag 230 includes a cinch cord, or tab (not shown), which may be translated to cinch closed the open end 238 of the bag 230. Alternatively, the bag 230 may be closed by any other suitable mechanism, e.g., thermal sealing by a forceps "F" (see FIG. 2). The closed bag 230 isolates the specimen from the body during removal, thus inhibiting seeding. The pre-formed glove portion 240 of the bag 230 acts as a pocket for collecting fluids trapped within the bag 230, reducing the potential for balling during removal. The bag 230 may be removed through the shaft 210, as shown in FIG. 9, to protect the surrounding tissue and to reduce the likelihood of the bag 230 "catching" during removal. Alternatively, the shaft 210 may be completely removed and the bag 230 may simply be removed from the access port (not shown) or opening in tissue.

Figure 10:
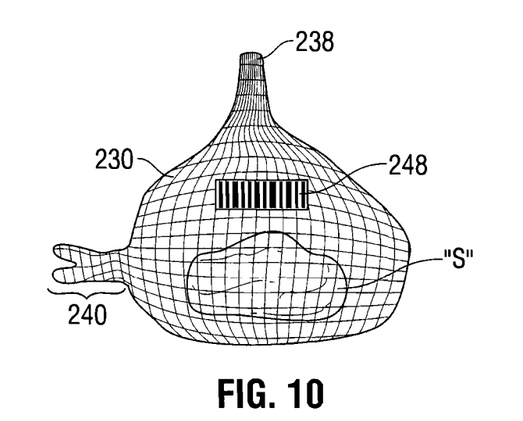
FIG. 10 is a side view of the bag including the tissue specimen disposed therein, showing a barcode pre-printed on the bag.
Figure 11:
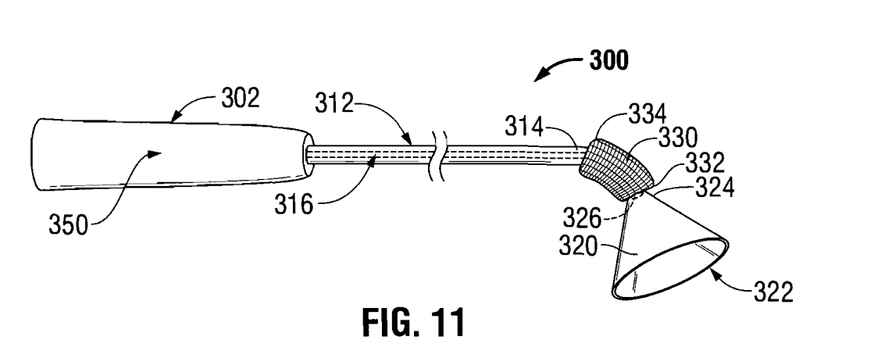
FIG. 11 is a side view of yet another specimen retrieval apparatus in accordance with the present disclosure.

FIG. 10 shows the bag 230 having the specimen "S" disposed therein once the bag 230 has been removed. The bag 230 optionally includes a pre-printed bar code 248 on the outer surface thereof to assist in the identification and tracking of the specimen "S" once it has been removed from the body.

Turning now to FIGS. 11-14, another embodiment of a specimen retrieval apparatus in accordance with the present disclosure is shown generally indicated by reference numeral 300. Specimen retrieval apparatus 300 includes a handle assembly 302, an elongated shaft 312, a suction cone 320, and a specimen retrieval bag 330. The elongated shaft 312 includes a lumen 316 therethrough. The elongated shaft 312 is formed from a semi-rigid material and extends from the handle assembly 302. The elongated shaft 312 can include an articulating distal end 314 to facilitate positioning of the suction cone 320 within the body. The specimen retrieval bag 330 is initially disposed at the distal end 314 of the elongated shaft 312 in an un-deployed, or retracted position. The bag 330 is selectively deployable to encapsulate a tissue specimen "S." The suction cone 320 is releasably engaged to the distal end 314 of the elongated shaft 312 and extends therefrom to an open distal end 322 of the suction cone 320. The suction cone 320 includes an aperture 326 defined at an apex, or proximal end 324 thereof.

The handle assembly 302 may include a two-way vacuum assembly 350 disposed therein or coupled thereto. The two-way vacuum assembly 350 may include, for example, a mechanical vacuum assembly, e.g., a hand pump and/or a foot pedal, or an electro-mechanical vacuum assembly. The two-way vacuum assembly 350 is configured to operate in a suction mode, for suctioning the tissue specimen "S" to the suction cone 320, and in a pressure mode, for deploying the specimen retrieval bag 330 over the tissue specimen "S." As such, the two-way vacuum assembly 350 communicates with the lumen 316 extending through the elongated shaft 312 which communicates with aperture 326 defined within the proximal end 324 of suction cone 320. Accordingly, when vacuum assembly 350 is operating in the suction mode, a suction force is provided at the aperture 326 and through the lumen 316 to suction a tissue specimen "S" within the suction cone 320.

Handle assembly 302 may also include one or more controls (not shown) for activating the two-way vacuum assembly 350, for switching the vacuum assembly 350 between the suction and reverse suction modes, and/or for articulating the distal end 314 of the elongated shaft 312 to maneuver the suction cone 320 into position.

The specimen retrieval bag 330 is sealingly engaged at one end 332 to the distal end 314 of the elongated shaft 312. Upon deployment, the open end 334 of the specimen retrieval bag 330 is extended over the tissue specimen "S" and cinched closed to retain the tissue specimen "S" therein (see FIGS. 13-14).

Suction cone 320 may be formed from a flexible material to conform to the tissue specimen "S" suctioned thereto to enhance suction. Suction cone 320 is preferably collapsed, or compressed, initially such that specimen retrieval apparatus 300 may be inserted through a relatively small opening in tissue. The suction cone 320 may include a one-way valve 362 disposed at the proximal end 324 thereof to permit suction therethrough. The one-way valve 362 is also configured to inhibit fluid from escaping the suction cone 320, such that the tissue specimen "S" may remain suctioned to the suction cone 320 even after the vacuum assembly 350 has been deactivated or transitioned to the pressure mode. Additionally, the suction cone 320 is preferably releasably coupled to the elongated shaft 312. The suction cone 320 may be releasable, for example, by activation of a trigger or other control member (not shown) disposed on the handle assembly 302.

Figure 12:
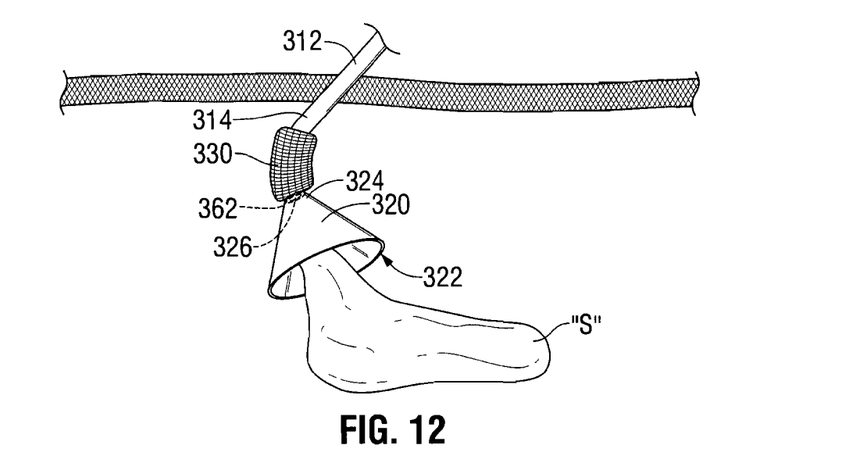
FIG. 12 is a side, cross-sectional view of the specimen retrieval apparatus of FIG. 11 shown disposed within a patient's body and suctioning a tissue specimen to a suction cone.

The operation of specimen retrieval apparatus 300 will now be described with reference to FIGS. 11-14. Initially, the elongated shaft 312, lead by the suction cone 320, is inserted through an access port (not shown) or opening in tissue, as shown in FIG. 12. As mentioned above, the suction cone 320 is initially disposed in a collapsed state (not shown). Suction cone 320 may be expanded (automatically or manually) from the initially state once elongated shaft 312 has been inserted through an opening in tissue. A control member, e.g., a joystick (not shown), disposed on the handle assembly 302 may be used to expand suction cone 320 and/or to articulate the distal end 314 of the elongated shaft 312 to position the suction cone 320 adjacent a tissue specimen "S" to be retrieved. With the suction cone 320 in position, the two-way vacuum assembly 350 is activated to operate in the suction mode, providing a suction force at the aperture 326 of the suction cone 320 such that the tissue specimen "S" is suctioned up into the funnel-shaped suction cone 320 and retained therein, as best shown in FIG. 12. The tissue specimen "S" may then be moved into position for deployment of the specimen retrieval bag 330 by manipulating the articulating distal end 314 of the elongated shaft 312 and/or by using a surgical grasper (not shown).

Figure 13:
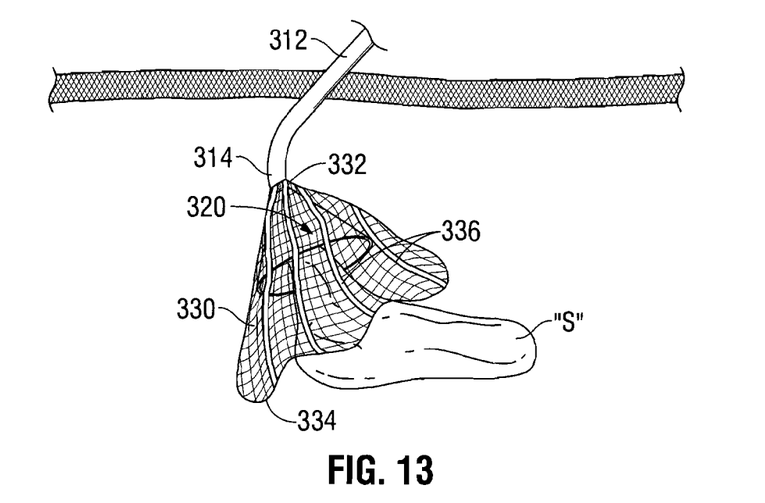
FIG. 13 is a side, cross-sectional view of the specimen retrieval apparatus of FIG. 11 showing a specimen retrieval bag being deployed over the tissue specimen.
Figure 14:
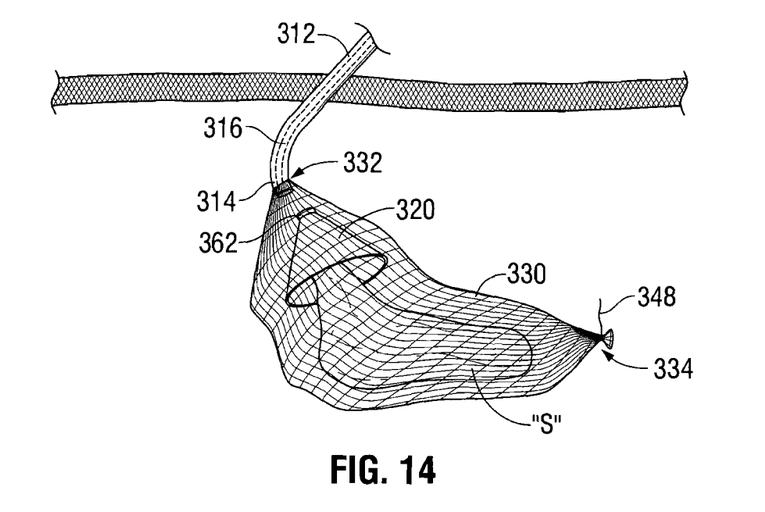
FIG. 14 is a side, cross-sectional view of the specimen retrieval apparatus of FIG. 11 wherein the bag has been fully deployed and cinched closed around the tissue specimen.

Once the tissue specimen "S" is in position as described above, the two-way vacuum may be switched from the suction mode to the pressure mode. Simultaneously with the deactivation of the suction mode, the one-way valve 362 operates to inhibit fluid from escaping or entering the aperture 326 of the suction cone 320, thus maintaining the suctioned relationship between the suction cone 320 and the tissue specimen "S." Accordingly, the two-way vacuum assembly 350 may be switched to the pressure mode, while the tissue specimen "S" is retained in position suctioned to the suction cone 320. In the reverse suction mode, fluid is urged through lumen 316 of elongated shaft 312 to inflate chambers 336 defined within the surface of specimen retrieval bag 330 (FIG. 13). As the chambers 336 are inflated, the specimen retrieval bag is deployed distally from the distal end 314 of the elongated shaft 312. The chambers 336 of the specimen retrieval bag 330 are inflated until the specimen retrieval bag 330 is substantially deployed over the tissue specimen "S," at which time the two-way vacuum 350 may be deactivated. A surgical grasper (not shown) may then be used to further manipulate the bag 330 around the tissue specimen "S." Next, as shown in FIG. 14, the open end 334 of the bag 330 may be sealed, tied-off, or cinched closed, e.g., via translation of cinch cord 348, to seal the tissue specimen "S" within the bag 330.

At this point, the previously open end 334 of the bag 330 has been closed, e.g., by cinch cord 348, and the other end 332 of the bag 330 remains sealingly engaged to the distal end 314 of the elongated shaft 312. Thus, the specimen "S" is fully encapsulated within the bag 330. Next, the suction cone 320 may be released, or detached from the elongated shaft 312, as shown in FIG. 14. Detachment of the suction cone 320 allows the suction cone 320 and the tissue specimen "S" to drop into the specimen retrieval bag 330. However, as shown in FIG. 14, the tissue specimen "S" is maintained within the sealed bag 330.

The two-way vacuum assembly 350 may then be re-activated to operate in the suction mode. The suction force at the distal end 314 of the elongated shaft 312 acts to reduce the volume inside the bag 330, or "shrink-wrap" the bag 330 about the tissue specimen "S" to facilitate removal. Suction cone 320 may be configured to automatically collapse back to the initial, or collapsed state upon shrink-wrapping of the specimen retrieval bag 330 to further reduce the volume of specimen retrieval bag 330. A grasper (not show), or other surgical instrument, may be used if desired to assist in the formation of the bag 330 in the desired shape for removal. The shaft 312 may then be translated proximally through the opening in tissue to remove the bag 330 from the internal body cavity.

Figure 15:
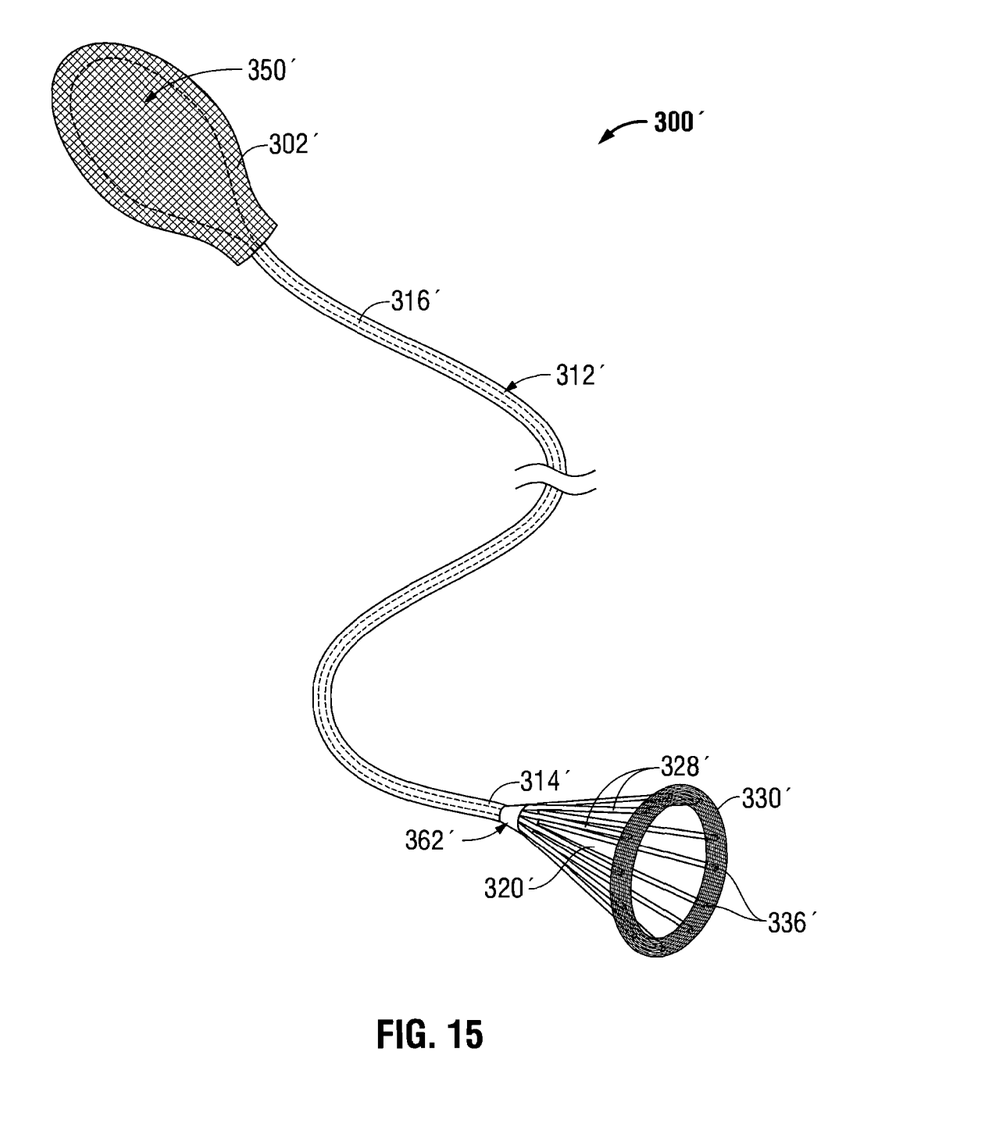
FIG. 15 is a perspective view of still yet another embodiment of a specimen retrieval apparatus in accordance with the present disclosure.

Turning now to FIG. 15, an alternate embodiment of the specimen retrieval apparatus 300 is shown generally designated by the reference numeral 300'. Specimen retrieval apparatus 300' is similar to specimen retrieval apparatus 300 and includes a handle 302', an elongated flexible tube 312' having a lumen 316' therethrough, an expandable suction cone 320' releasably disposed at a distal end 314' of the elongated tube 312', and a deployable specimen retrieval bag 330' initially disposed on the suction cone 320' toward a distal end thereof.

Handle assembly 302' may include a hand pump 350' and/or a foot pump (not shown) for providing suction and/or pressure through the lumen 316'. As can be appreciated, repeated squeezing and releasing of hand pump 350' provides a suctioning effect at suction cone 320' to retain a tissue specimen "S" thereon. A switch or tab may be provided to transition the hand pump 350' between the suction mode and the pressure mode. Alternatively, the hand pump 350' may be configured for suction and thus, may be detachable from the elongated tube 312'. As such, a reverse suction mechanism, e.g., a foot pedal (not shown), may be coupled to the elongated tube 312' to provide reverse suction.

A one-way valve 362', similar to one-way valve 362, is positioned on the apex of the elongated tube 312'. The one-way valve 362' inhibits the loss of suction when the hand pump 350' is deactivated, detached, or otherwise not providing a suction force to the suction cone 320'.

As shown in FIG. 15, one or more fluid channels 328' extend distally along an outer surface of the suction cone 320'. Channels 328' communicate with inflation chambers 336' of specimen retrieval bag 330'.

In operation, with the suction cone 320' initially disposed in the collapsed state, the elongated tube 312' is inserted through an opening in tissue and the suction cone 320' is positioned adjacent a tissue specimen "S" to be retrieved. The suction cone 320' may then automatically (or manually) expand to the position shown in FIG. 15. The hand pump 350', or other vacuum mechanism is then activated to suction the tissue specimen "S" to the suction cone 320'. The hand pump 350' may then be disengaged, and the foot pump (not shown) or other vacuum assembly may be attached to the elongated tube 312' for providing reverse suction. As mentioned above, the one-way valve 362' retains the suctioned relationship between the tissue specimen "S" and the suction cone 320' when the vacuum assembly 350' is not suctioning. During reverse suction, the channels 328' extending along the suction cone 320' inflate the chambers 336' of specimen retrieval bag 330' to deploy the specimen retrieval bag 330' over the tissue specimen "S."

As in the previous embodiment, once the chambers 336' are fully inflated, i.e., once the bag 330' is fully deployed, the open end of the bag 330' may then be cinched closed to seal the tissue specimen "S" within the bag 330'. The hand pump 350' or other vacuum assembly (not shown) may then be re-activated to suction, or "shrink-wrap" the bag 330' about the tissue specimen "S." Finally, the suction cone 320' may be released from the elongated tube 312' and the specimen retrieval bag 330' may be removed from the access port (not shown) or opening in tissue via a surgical grasper or other suitable surgical instrument.

In some embodiments, the elongated tube 312' may be made from a flexible material but configured to retain its shape. In other words, the elongated tube 312' would be manipulatable to position the suction cone 320' adjacent the tissue specimen "S" and, once in position, would maintain that shape such that the suction cone 320' is maintained in position adjacent the tissue specimen "S." Such a feature would allow the specimen retrieval apparatus 300' to be "snaked" around and through complex openings in tissue. Additionally, the elongated tube 312' may incorporate illumination, e.g., a chemical snap-to-light (not shown), to provide better visualization of the elongated tube 312' within the body cavity.

Figure 16:
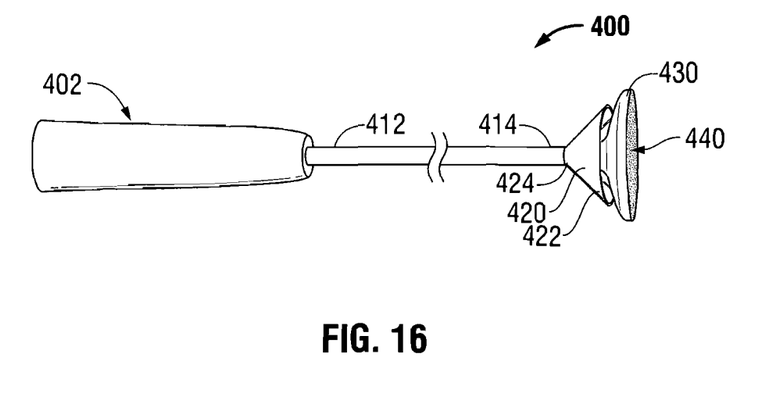
FIG. 16 is a side view of a surgical retraction apparatus in accordance with the present disclosure.
Figure 17:
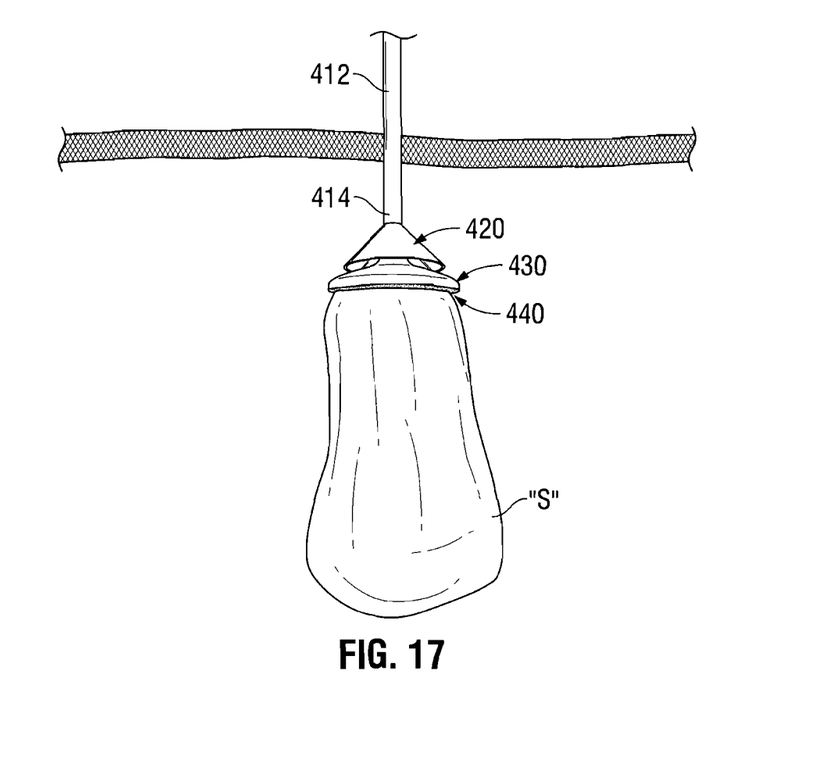
FIG. 17 is a side, cross-sectional view of the retraction apparatus of FIG. 16 showing an adhesive patch adhering the tissue specimen to the retraction apparatus.

Referring now to FIGS. 16-17, a specimen retraction apparatus is also provided in accordance with another embodiment of the present disclosure. The apparatus is generally 400 includes a handle assembly 402, an elongated shaft 412, and a grasping portion 420 including a grasping member 430. An adhesive patch 440 is disposed on a surface of the grasping member 430 to adhere a tissue specimen "S" to the grasping member 430.

The elongated shaft 412 extends from the handle assembly 402 and may be made from a rigid or a semi-rigid material. The grasping portion 420 is generally cone-shaped and is engaged at an apex 424 thereof to a distal end 414 of the elongated shaft 412. The grasping member 430 extends from a distal end 422 of the grasping portion 420. The grasping member 430 may be made from a flexible material to conform to the surface geometry of a particular specimen "S." The grasping member 430 is preferably collapsible, or sufficiently flexible to permit insertion of the apparatus 400 through relatively small openings in tissue.

The adhesive patch 440 is preferably made from a relatively thin, tear-resistant material and is positionable on the surface of the grasping member 430. It is envisioned that the adhesive patch 440 be releasably coupled to the grasping member 430.

In use, the elongated shaft 412 is inserted through an access port (not shown) or an opening in tissue such that the grasping portion 420 is positioned adjacent a tissue specimen "S" to be retracted. The elongated shaft 412 is then moved to engage, or mate the grasping member 430, having the adhesive patch 440 disposed thereon, with the surface of the tissue specimen "S." Pressure is applied distally to ensure proper adhesion of the adhesive patch 440 to the tissue specimen "S." As mentioned above, the flexible grasping member 430 may conform to the tissue specimen "S" to adhere the adhesive patch 440 consistently along the surface of the tissue specimen "S."

Once adhered to the tissue specimen "S," the specimen "S" may be retracted by manipulating the elongated shaft 412. The elongated shaft 412 may include an articulating portion (not show) or, alternatively, the grasping portion 420 may be configured to articulate relative to the elongated shaft 412 to provide for greater maneuverability.

The tissue specimen "S" may be retracted, for example, to provide greater access to underlying tissue or to position the tissue specimen "S" for resection. When the desired procedure is complete, the adhesive patch 440 may be released from the grasping member 430. It is envisioned that the adhesive patch 440 be made from a bio-material such that the adhesive patch 440 may be left behind to be absorbed by the body. Accordingly, once the adhesive patch 440 has been released, the device 400 may be removed from the opening in tissue.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A specimen retrieval apparatus comprising:

an elongated tubular member defining a lumen extending therethrough and having a proximal end and a distal end;

a vacuum assembly coupled to the proximal end of the elongated tubular member and in communication with the lumen extending therethrough, the vacuum assembly configured for operation in each of a suction mode and a pressure mode;

a suction cone disposed at the distal end of the elongated tubular member, the suction cone defining an aperture at an apex thereof, the aperture in fluid communication with the lumen of the elongated tubular member, the suction cone configured to suction a tissue specimen thereto when the vacuum assembly is operating in the suction mode; and a specimen retrieval bag disposed at a distal end of the elongated tubular member, the bag being inflatable from an un-deployed state to a deployed state to surround the suction cone and specimen retained by the suction cone when the vacuum assembly is operating in the pressure mode.

2. The specimen retrieval apparatus according to claim 1, wherein the suction cone is releasably coupled to the distal end of the elongated tubular member.

3. The specimen retrieval apparatus according to claim 1, wherein the bag is sealingly engaged at a first end to the elongated tubular member.

4. The specimen retrieval apparatus according to claim 1, wherein the suction cone is collapsible for insertion.

5. The specimen retrieval apparatus according to claim 1, wherein the vacuum assembly is operable in the suction mode subsequent to the pressure mode to reduce the volume within the bag and collapse the bag.

\* \* \* \* \*